(12) United States Patent
DeLucia et al.

(10) Patent No.: US 6,653,524 B2
(45) Date of Patent: Nov. 25, 2003

(54) NONWOVEN MATERIALS WITH TIME RELEASE ADDITIVES

(75) Inventors: Mary Lucille DeLucia, Roswell, GA (US); Robert Leslie Hudson, Las Vegas, NV (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/729,655

(22) Filed: Dec. 4, 2000

(65) Prior Publication Data

US 2001/0031938 A1 Oct. 18, 2001

Related U.S. Application Data

(60) Provisional application No. 60/171,962, filed on Dec. 23, 1999.

(51) Int. Cl.[7] .................................................. A61F 13/15
(52) U.S. Cl. ......................................... 604/367; 604/364
(58) Field of Search ........................... 604/359, 360, 604/361, 362, 367, 364; 424/400, 402, 489, 76.5, 76.6

(56) References Cited

U.S. PATENT DOCUMENTS

| | | | |
|---|---|---|---|
| 3,018,264 A | 1/1962 | Colclough, Jr. | |
| 3,054,769 A | 9/1962 | Pike | |
| 3,245,946 A | 4/1966 | O'Connor et al. | |
| 3,338,992 A | 8/1967 | Kinney | |
| 3,341,394 A | 9/1967 | Kinney | |
| 3,341,488 A | 9/1967 | O'Connor | |
| 3,382,199 A | 5/1968 | Scullin | |
| 3,502,763 A | 3/1970 | Hartmann | |
| 3,542,615 A | 11/1970 | Dobo et al. | |
| 3,644,273 A | 2/1972 | Mills | |
| 3,692,618 A | 9/1972 | Dorschner et al. | |
| 3,802,817 A | 4/1974 | Matsuki et al. | |
| 3,849,241 A | 11/1974 | Butin | |
| 4,340,563 A | 7/1982 | Appel et al. | |
| 4,420,341 A | 12/1983 | Ferrigno | |
| 4,432,802 A | 2/1984 | Harata et al. | |
| 4,529,750 A | 7/1985 | Gimpel | |
| 4,722,815 A | 2/1988 | Shibanai | |
| 4,775,585 A | 10/1988 | Hagiwara et al. | |
| 4,781,858 A | 11/1988 | Mizukami et al. | |
| 4,795,668 A | 1/1989 | Krueger et al. | |
| 4,853,426 A | 8/1989 | Chatterjee | |
| 4,879,141 A | 11/1989 | Chatterjee | |
| 4,938,958 A | 7/1990 | Niira et al. | |
| 4,959,268 A | 9/1990 | Hagiwara et al. | |
| 5,057,368 A | 10/1991 | Largman et al. | |
| 5,069,970 A | 12/1991 | Largman et al. | |
| 5,108,820 A | 4/1992 | Kaneko et al. | |
| 5,194,457 A | 3/1993 | Brichta et al. | |
| 5,208,275 A | 5/1993 | Chatterjee | |
| 5,277,976 A | 1/1994 | Hogle et al. | |
| 5,336,552 A | 8/1994 | Strack et al. | |
| 5,376,698 A | 12/1994 | Sipsas et al. | |
| 5,382,400 A | 1/1995 | Pike et al. | |
| 5,384,186 A | 1/1995 | Trinh | |
| 5,429,628 A | * 7/1995 | Trinh et al. .................. 604/359 |
| 5,466,410 A | 11/1995 | Hills | |
| 5,482,989 A | 1/1996 | Koskiniemi | |
| 5,492,947 A | 2/1996 | Wood et al. | |
| 5,498,478 A | * 3/1996 | Hansen et al. ............... 428/372 |
| 5,540,992 A | 7/1996 | Marcher et al. | |
| 5,571,096 A | * 11/1996 | Dobrin et al. ............... 604/383 |
| 5,591,146 A | * 1/1997 | Hasse .......................... 604/359 |
| 5,603,974 A | 2/1997 | Wood et al. | |
| 5,718,905 A | 2/1998 | Skiba et al. | |
| 5,769,833 A | * 6/1998 | Hasse .......................... 604/359 |
| 5,844,033 A | 12/1998 | Nikkeshi et al. | |
| 5,855,571 A | * 1/1999 | Steger et al. ................ 604/368 |
| 5,869,551 A | 2/1999 | Caswell et al. | |
| 5,951,534 A | * 9/1999 | Cummings et al. .......... 604/359 |
| 6,229,062 B1 | * 5/2001 | Mandell et al. ............. 604/367 |

FOREIGN PATENT DOCUMENTS

| | | |
|---|---|---|
| EP | 186 146 | 7/1986 |
| FR | 2 665 169 | 1/1992 |
| JP | 108 922 | 5/1984 |
| JP | 1225 644 | 9/1989 |
| JP | 3014 678 | 1/1991 |
| WO | 98/26808 | 6/1998 |

* cited by examiner

Primary Examiner—Weilun Lo
Assistant Examiner—Jacqueline F. Stephens
(74) Attorney, Agent, or Firm—Pauley Petersen & Erickson

(57) ABSTRACT

A personal care absorbent article comprising a nonwoven material comprising at least one time release additive. Time release of additives is addressed by encapsulating the additive in a large cavity or cage molecule such as cyclodextrin or zeolite.

18 Claims, No Drawings

NONWOVEN MATERIALS WITH TIME RELEASE ADDITIVES

CROSS REFERENCE TO RELATED APPLICATION

This application claims the benefit of U.S. Provisional Application No. 60/171,962, filed Dec. 23, 1999.

BACKGROUND OF THE INVENTION

1. Field of the Invention

This invention relates to nonwoven materials comprising time release additives, which nonwoven materials are used in the production of personal care absorbent articles such as diapers, training pants, incontinence garments, and feminine care products such as sanitary pads and panty liners, health care products including surgical gowns and drapes, surgical wraps, wound dressings, fenestration reinforcement materials, industrial wipes, work wear and the like. The time release additives may be added to the polymeric materials used in the manufacture of the nonwoven materials or they may be added as a surface treatment to the nonwoven materials. The time release additives may be used to impart a feature that is deficient in the polymeric material, or they may be used to impart a feature to the nonwoven materials upon being activated or triggered by an event such as an insult.

2. General Background

The use of cage molecules as a means for controlling the release of a desired property over an extended period of time is well-known in the art. Cage molecules are molecules that contain cavities or interstitial spaces which may be used to entrap materials for a wide variety of applications. Such cage molecules which have been used include zeolites and cyclodextrin.

U.S. Pat. No. 5,603,974 teaches a barrier film composition comprising a thermoplastic web comprising a thermoplastic polymer and dispersed cyclodextrin composition having substituents that compatibilize the cyclodextrin in the film. The thermoplastic/cyclodextrin film obtains substantial barrier properties from the interaction between the substituted cyclodextrin in the film material with a permeant. In this case, the permeant is complexed or entrapped by the cyclodextrin compound and held within the film, thereby preventing the permeant from passing through the film into the interior of a film, an enclosure or container.

U.S. Pat. No. 5,844,033 teaches a polycarbonate resin composition comprising substantially a polycarbonate resin and zeolite having tannic adsorbed thereon, wherein the molecular weight reduction (that is, quality deterioration) of the polycarbonate resin caused by its decomposition is suppressed by the inclusion of zeolite (having adsorbability and slow releasability) having tannic acid (a polyhydric phenol compound) adsorbed thereon.

U.S. Pat. No. 5,384,186 teaches solid consumer products (compositions) containing solid cyclodextrin inclusion complexes of actives, which are typically hydrophobic materials like perfumes, flavoring materials, pharmaceutical actives, antibacterials, bleaches and the like, which products/compositions are either in particulate form, compounded with other materials in solid form, such as tablets, pellets, agglomerates and gel sticks, or attached to a substrate.

U.S. Pat. No. 4,722,815 teaches a synthetic resin product containing various substances selected from among perfumes, insectifuges, rust preventive, mildewproofing and bactericide which are inactivated by forming an inclusion compound thereof in cyclodextrin and coating them with glycitols to thereby prolong the duration period of the substance.

U.S. Pat. No. 3,341,488 teaches the release of materials such as active chemicals contained in the inner adsorption region of crystalline zeolitic molecular sieves in a reaction zone where they may, for example, serve as curing agents for rubber formulations, epoxy resins or as catalysts for the formation of polyurethane foams.

See also, French patent publication 2,665,169 which teaches cyclodextrin containing compounds containing phenolic antioxidants for heat stabilizing polymers such as polypropylene and Japanese Patent Abstract JP-108922 which teaches long life anti-rust agents comprising thermoplastic resins containing cyclodextrin inclusion compounds of vaporisable anti-rust agents. No benefit from a time release perspective is seen from the encapsulation of phenolic antioxidants as taught by the '169 French publication because any phenolic antioxidants which are employed are immediately consumed as the result of an activating event.

Although this technology is well known for use in connection with a variety of applications, none of the applications relate to its use in connection with personal care absorbent articles. Such applications may include the time release of compounds for odor control, for fluid distribution control on an as needed basis, for application of medicaments over time, and generally for controlled delivery of additives used in such products and for photostabilization of polymers employed in materials such as car seat covers.

SUMMARY OF THE INVENTION

It is one object of this invention to provide a method for controlling the delivery of additives used in personal care absorbent articles, including, but not limited to, disposable diapers, training pants, incontinence garments, feminine hygiene products, health care products and industrial fabrics.

It is another object of this invention to control the benefit derived from additives to personal care absorbent articles, for example, to extend the period over which the benefit may derived or to render the benefit upon the occurrence of an activation event.

These and other objects of this invention are addressed by a nonwoven material comprising at least one time release additive, which nonwoven material is suitable for use in personal care absorbent articles including disposable diapers, training pants, incontinence garments, feminine hygiene products, health care products and industrial fabrics. Such personal care absorbent articles typically comprise a cover sheet and a back sheet, at least one of said cover sheet and said back sheet comprising a time release additive. In accordance with one embodiment of this invention, an absorbent core is disposed between said cover sheet and said back sheet, in which case the time release additive may be disposed within the absorbent core. Time release of additives in accordance with one embodiment of this invention is achieved by encapsulating the additive in a controlled release material selected from the group consisting of zeolites, cyclodextrin, cage molecules, natural and synthetic minerals and combinations thereof.

In accordance with one preferred embodiment of this invention, at least one of the cover sheet, the back sheet and the absorbent core comprises a film, a nonwoven material or a laminate comprising at least one polymeric material. The encapsulated additive may be disposed on the surface of the cover sheet, the back sheet and/or the absorbent core, and/or in the interior of the cover sheet, the back sheet and/or the absorbent core, and/or incorporated into the polymer used to produce the cover sheet, the back sheet and/or the absorbent core.

DESCRIPTION OF PREFERRED EMBODIMENTS

Definitions

As used herein, the term "comprising" is inclusive or open-ended and does not exclude additional unrecited elements, compositional components, or method steps.

As used herein, the term "nonwoven web" means a web that has a structure of individual fibers or threads which are interlaid, but not in an identifiable repeating manner. Nonwoven webs have been, in the past, formed by a variety of processes such as, for example, meltblowing processes, spunbonding processes, coforming processes, hydroentangling, air-laid and bonded carded web processes.

As used herein, the term "spunbond fibers" refers to small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10 fibers) larger than 7 microns, more particularly, between about 10 and 30 microns. The fibers may also have shapes such as those described in U.S. Pat. No. 5,277,976 to Hogle et al., U.S. Pat. No. 5,466,410 to Hills, and U.S. Pat. Nos. 5,069,970 and 5,057,368 to Largman et al., which describe hybrids with unconventional shapes. A nonwoven web of spunbond fibers produced by melt spinning is referred to as a "spunbond".

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, by U.S. Pat. No. 3,849,241 to Butin et al. Meltblown fibers are microfibers which may be continuous or discontinuous, and are generally smaller than 10 microns in average diameter.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker or fiberizer which separates the fibers prior to the carding unit. Once the web is formed, it is then bonded by one or more of several known bonding methods.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" also includes all possible geometric configurations of the molecule. These configurations include, but are not limited to, isotactic, atactic, syndiotactic and random symmetries.

As used herein, the term "microfibers" refers to small diameter fibers having an average diameter not greater than about 100 microns, for example, having an average diameter of from about 0.5 microns to about 50 microns, or more particularly, having an average diameter of from about 2 microns to about 40 microns. Another frequently used expression of fiber diameter is denier, which is defined as grams per 9000 meters of a fiber, and may be calculated as fiber diameter in microns squared, multiplied by the density in grams/cc, multiplied by 0.00707. A lower denier indicates a finer fiber and a higher denier indicates a thicker or heavier fiber. For example, a diameter of a polypropylene fiber given as 15 microns may be converted to denier by squaring, multiplying the results by 0.89 g/cc and multiplying by 0.00707. Thus, a 15 micron polypropylene fiber has a denier of about 1.42. Outside the United States, the unit of measurement is more commonly the "tex", which is defined as the grams per kilometer of fiber. Tex may be calculated as denier/9.

As used herein, the term "blend" means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein, the term "bicomponent fibers" refers to fibers which have been formed from at least two polymers extruded from separate extruders but spun together to form one fiber. Bicomponent fibers are also sometimes referred to as conjugate fibers or multicomponent fibers. The polymers are arranged in substantially constantly positioned distinct zones across the cross-sections of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement. Bicomponent fibers are taught by U.S. Pat. No. 5,108,820 to Kaneko et al., U.S. Pat. No. 4,795,668 to Krueger et al., U.S. Pat. No. 5,540,992 to Marcher et al., and U.S. Pat. No. 5,336,552 to Strack et al. Bicomponent fibers are also taught by U.S. Pat. No. 5,382,400 to Pike et al. For two component fibers, the polymers may be present in ratios of 75/25, 50/50, 25/75 or any other desired ratio.

As used herein, the term "personal care absorbent article" means disposable diapers, training pants, absorbent underpants, adult incontinence products, feminine hygiene products including sanitary pads and napkins, wipes, tissues, bandages, dressings, surgical gowns and drapes, industrial work wear and the like.

As used herein, the term "absorbent material" refers to any material having fluid absorption properties.

Additives may be added to personal care absorbent articles for a variety of reasons, including fluid distribution control, odor control, staining control and the like. This invention provides a means by which the benefits which may be realized from the presence of the additives may be controlled so as to be provided only when needed, as in the case of a disposable diaper or sanitary pad or tampon exposed to multiple insults during a single use, or on a continuous basis throughout the useful life of the product. This invention also provides a means for imparting a feature to the polymers used to produce articles such as car seat covers which are regularly exposed to light in which the polymer is deficient, such as the addition of photostabilizers. Upon exhaustion of the additive, the feature disappears and the deficiency of the polymer is displayed.

This invention involves sequestering the additive in an environment in which it would be released over time on an as needed basis, which may be periodic or continuous. The additive is encapsulated in a larger molecule, which under a given set of conditions, or on a continuous basis, releases the additive to perform its beneficial function.

Any molecule having a cavity of appropriate geometry or chemistry may be utilized for encapsulation of the additive of choice. Molecules that contain cavities are available from a number of chemical supply houses and other vendors. In accordance with one embodiment of this invention, the encapsulating molecule is a naturally occurring zeolite (molecular sieve). In addition to encapsulation of a desired additive, inorganic molecules such as zeolite impart an aesthetic hand to nonwoven fabrics. In accordance with another embodiment of this invention, the encapsulating molecule is a large-cage molecule having a zeolite structure. As used herein, the term "zeolite structure," refers to large-pore structures having interconnecting channels. Such structures are the subject of crystallographic studies described in the literature (Xianhui Bu, Science, Vol. 278, December 1997). In accordance with yet another embodiment of this invention, the encapsulating molecule is cyclodextrin. Cyclodextrin (CAVIRON®840N0, 800N0, and 820N0) is available from CERESTAR®. In accordance with yet a further embodiment of this invention, the encapsulating molecules are natural and/or synthetic minerals.

As previously stated, personal care absorbent articles in accordance with this invention comprise a cover sheet, a back sheet and, in many instances, an absorbent core. Each of these components performs one or more functions within the personal care absorbent article.

Cover sheet materials are utilized for the transport of bodily fluids into the absorbent core of personal care absorbent articles and, thus, materials used for cover sheet applications must manage distinctly different body excretions, depending upon the application and the product type. Some products must manage fluids, such as urine, while others must manage proteinaceous and viscoelastic fluids such as menstrual discharge and fecal matter. The management of viscoelastic menstrual discharge by cover sheet materials for feminine care products is exacerbated due to the variations in composition and rheology over a broad range of elasticity. Fluid management in feminine care applications requires control of absorption of bodily fluids, control of fluid retention in the cover, control of stain size and intensity, control of rewet of fluid back to the surface, and control of the release of fluid to the absorbent core.

The absorbent material is used to absorb and hold or contain body fluids. The movement of fluid away from the target zones requires the presence of two key functionalities—1) fluid handling or "distribution" throughout the entire product length and width and 2) "slow absorption" retention material located in the target zone. A slow absorbing retention material has the potential for higher absorbency rates while reducing product performance deterioration typically associated with later insults. Improved fluid handling may be achieved by application of a surfactant treatment system which imparts an enhanced fluid intake rate on multiple insults and a significantly durable hydrophilic character.

The back sheet is used to contain the fluids within the personal care absorbent article and normally comprises a material having barrier properties which prevents the passage of fluid therethrough.

For each of these components, there are a variety of methods known to those skilled in the art for enhancing the functionality of each component. Frequently, these include the treatment of the materials comprising these components with chemical systems designed to address a certain aspect of the functionality such as the use of surfactants to promote hydrophilicity, or the use of superabsorbents to provide long term absorbency. These systems may be deployed on the surfaces of the materials, for example the surfaces of the polymeric fibers which make up nonwoven materials, or directly in the polymer itself.

In the latter case, the treatment system is added to the polymer prior to extrusion. Accordingly, suitable encapsulating molecules for use in this type of application must be able to withstand extrusion conditions. Organic materials, in low concentration, can withstand extrusion conditions. Inorganic materials can withstand extrusion conditions even at high (10% by weight) concentrations. In addition, the encapsulating molecules or vehicles must be able to withstand the elevated temperatures at which the polymers are processed. In accordance with one embodiment of this invention, only an encapsulated additive is compounded into the polymer. In accordance with another embodiment of this invention, an additive may be compounded into the polymer both in encapsulated form and in conventional form.

Another consideration regarding the choice of encapsulating vehicle is the size and shape of the particular additive. Thus, the cavities and channels comprising the structure of the encapsulating vehicle must be matched to the size and shape of the additives required for providing a desired benefit.

The ratio of the amount of an encapsulating vehicle to the amount of additive is preferably calculated on the basis of stoichiometry. However, when calculation is not practical, the ratio may be determined empirically. This ratio is a function of the active groups of the encapsulating vehicle and the additive. In accordance with one preferred embodiment, less than about 5% by weight of the encapsulating vehicle is required for encapsulation of an additive. This may, however, vary depending upon the number of active sites of the vehicle.

In order to be effective as a time release device, a means for activating the release of the additive is required. In accordance with one embodiment of this invention, the actuation means is a concentration gradient across the encapsulating vehicle and the polymer in which the encapsulated additive is disposed. For example, the actuation means may be the concentration differential of an additive between the cavity of the encapsulating vehicle and the polymer. In accordance with other embodiments, a more complex agent such as water, heat or chemical treatment may be employed as an activation means. In accordance with still other embodiments, activation is the result of contact with one or more body exudates including, urine, menses and blood. In general, the activation means employed is driven by the particular application.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A personal care absorbent article comprising:
   a cover sheet and a back sheet, at least one of said cover sheet and said back sheet comprising an encapsulating vehicle and a time release additive in the encapsulating vehicle;
   wherein release of said time release additive from the encapsulating vehicle is activated by a concentration differential of said time release additive across the encapsulating vehicle.

2. A personal care absorbent article in accordance with claim 1 further comprising an absorbent core disposed between said cover sheet and said back sheet.

3. A personal care absorbent article in accordance with claim 2, wherein said time release additive is disposed in said absorbent core.

4. A personal care absorbent article in accordance with claim 2, wherein at least one of said cover sheet, said back sheet and said absorbent core comprises a nonwoven web.

5. A personal care absorbent article in accordance with claim 1, wherein said time release additive is encapsulated in a material selected from the group consisting of zeolites, cyclodextrin, cage molecules, natural minerals, synthetic minerals and combinations thereof.

6. A personal care absorbent article in accordance with claim 1, wherein activation of the release of the time release additive is triggered by an insult.

7. A material comprising:
   a nonwoven material comprising an encapsulating vehicle and at least one time release additive in the encapsulating vehicle;
   wherein release of said time release additive from the encapsulating vehicle is activated by a concentration differential of said time release additive across the encapsulating vehicle.

8. A material in accordance with claim 7, wherein activation of the release of the time release additive is triggered by an insult.

9. A material in accordance with claim 7, wherein said nonwoven material is selected from the group consisting of spunbonds, meltblowns, bonded carded webs, films, laminates and combinations thereof.

10. A material in accordance with claim 7, wherein said time release additive is encapsulated in a material selected from the group consisting of cyclodextrin, zeolites, large cage molecules, natural minerals, synthetic minerals and combinations thereof.

11. A diaper comprising:
    a fluid pervious top sheet, a fluid impervious outer cover and an absorbent core disposed between said fluid pervious top sheet and said fluid impervious outer cover, at least one of said fluid pervious top sheet, said fluid impervious outer cover, and said absorbent core comprising an encapsulating vehicle and at least one time release additive in the encapsulating vehicle;
    wherein release of said time release additive from the encapsulating vehicle is actuated by a concentration differential of said time release additive across the encapsulating vehicle.

12. A diaper in accordance with claim 11, wherein activation of the release of the time release additive is triggered by an insult.

13. A diaper in accordance with claim 11, wherein at least one of said fluid pervious cover sheet, said fluid impervious outer cover, and said absorbent core comprises a nonwoven web.

14. A diaper in accordance with claim 11, wherein said time release additive is encapsulated in a material selected from the group consisting of zeolites, cyclodextrin, cage molecules, natural minerals, synthetic minerals and combinations thereof.

15. A medical garment comprising:
    a nonwoven material comprising an encapsulating vehicle and at least one time release additive in the encapsulating vehicle, wherein release of said time release additive from the encapsulating vehicle is activated by a concentration differential of said time release additive across the encapsulating vehicle.

16. A medical garment in accordance with claim 15, wherein activation of the release of the time release additive is triggered by an insult.

17. A medical garment in accordance with claim 15, wherein said nonwoven material is selected from the group consisting of spunbonds, meltblowns, bonded carded webs, films, laminates and combinations thereof.

18. A medical garment in accordance with claim 15, wherein said time release additive is encapsulated in a material selected from the group consisting of cyclodextrin, zeolites, large cage molecules, natural minerals, synthetic minerals and combinations thereof.

* * * * *